(12) United States Patent
De Angelis et al.

(10) Patent No.: US 9,024,068 B2
(45) Date of Patent: May 5, 2015

(54) PROCESS FOR THE PREPARATION OF CRYSTALLINE FORMS OF AGOMELATINE AND NOVEL POLYMORPH THEREOF

(75) Inventors: Bruno De Angelis, Segrate (IT); Faris Garis, Segrate (IT); Salvatore De Gennaro, Segrate (IT); Giorgio Bertolini, Segrate (IT)

(73) Assignee: Laboratorio Chimico Internazionale S.p.A., Milan (IT)

( * ) Notice: Subject to any disclaimer, the term of this patent is extended or adjusted under 35 U.S.C. 154(b) by 0 days.

(21) Appl. No.: 14/126,731

(22) PCT Filed: Dec. 29, 2011

(86) PCT No.: PCT/IB2011/003176
§ 371 (c)(1),
(2), (4) Date: Feb. 17, 2014

(87) PCT Pub. No.: WO2012/172387
PCT Pub. Date: Dec. 20, 2012

(65) Prior Publication Data
US 2014/0221690 A1  Aug. 7, 2014

(30) Foreign Application Priority Data
Jun. 15, 2011 (IT) .............................. MI2011A1078

(51) Int. Cl.
C07C 231/12 (2006.01)
C07C 231/24 (2006.01)

(52) U.S. Cl.
CPC ............ *C07C 231/12* (2013.01); *C07C 231/24* (2013.01)

(58) Field of Classification Search
None
See application file for complete search history.

(56) References Cited

U.S. PATENT DOCUMENTS

| 5,194,614 A | 3/1993 | Andrieux et al. |
| 2011/0130571 A1 | 6/2011 | Zhang et al. |
| 2012/0252901 A1 | 10/2012 | Zhu et al. |

FOREIGN PATENT DOCUMENTS

| EP | 2 319 827 | 5/2011 |
| EP | 2 474 522 B1 | 7/2012 |

OTHER PUBLICATIONS

Abstract for CN 102229541, Nov. 2, 2011 publication.*
International Search Report for PCT/IB2011/003176, mailed May 29, 2012.
Written Opinion of the International Searching Authority for PCT/IB2011/003176, mailed May 29, 2012.
Italy Search Report for Italy Application MI20111078, dated Jan. 16, 2012.
Database WPI, "New agomelatine crystals used preparing pharmaceutical composition for preventing and treating diseases e.g. tension and sleep disorder, have X-ray powder diffraction pattern which shows specific characteristics diffraction peaks", & CN 102 050 755, (May 11, 2011), abstract.
European Patent Application No. 10838509.7 Reply to Search Opinion/Written Opinion/IPER; Amended claims with annotations; documents filed during examination procedure in relation to the prosecution of EP 2 474 522 B1; (Sep. 6, 2013) 11 pages.

* cited by examiner

*Primary Examiner* — Brandon Fetterolf
*Assistant Examiner* — Ana Z Muresan
(74) *Attorney, Agent, or Firm* — Nixon & Vanderhye P.C.

(57) ABSTRACT

The invention concerns a new process for the preparation of crystalline form of agomelatine from a solution of agomelatine in a solvent, characterized in that the agomelatine is crystallized by instantaneous precipitation from said solution, at a temperature equal to or below −10° C.

5 Claims, 1 Drawing Sheet

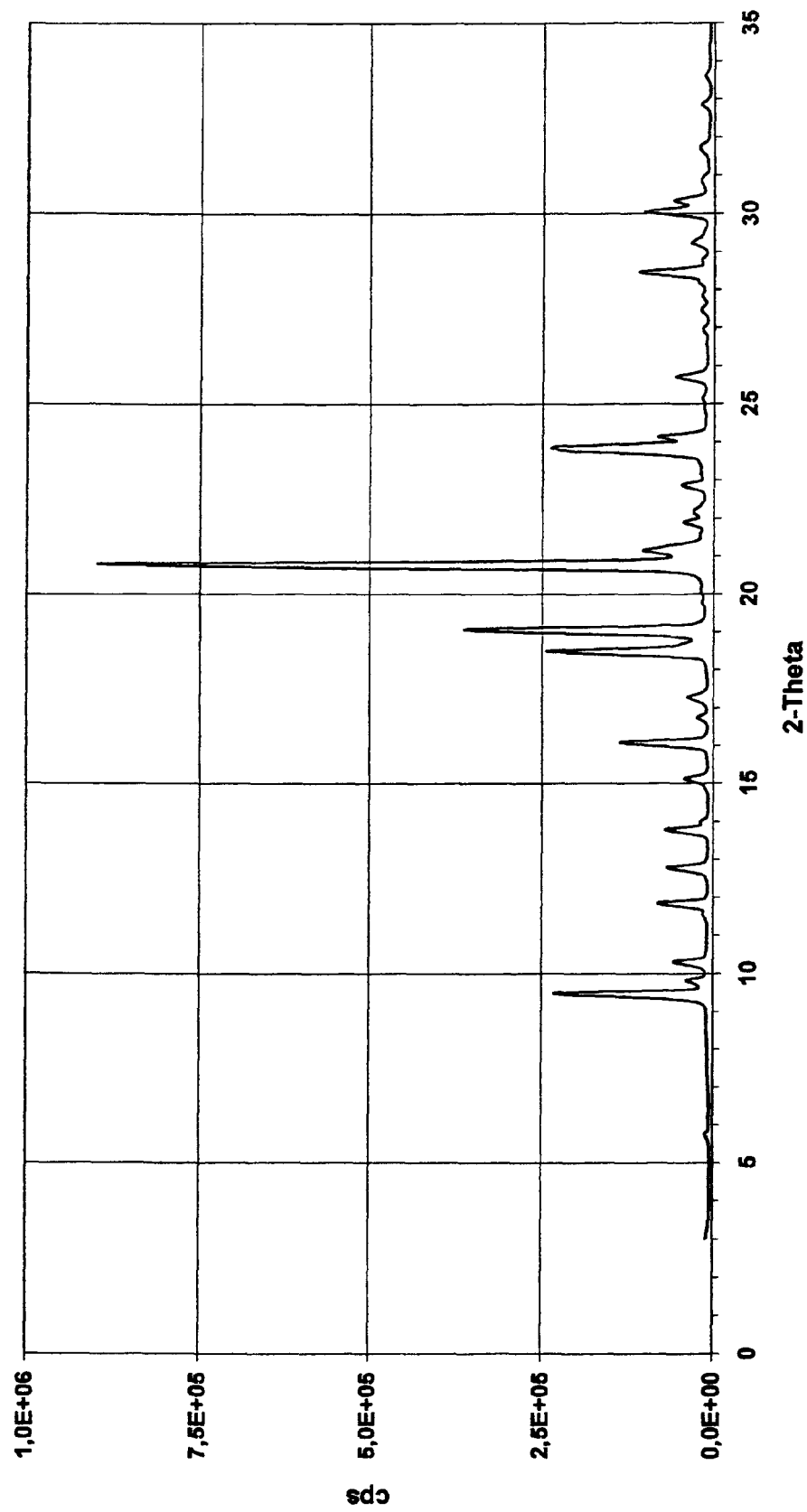

PROCESS FOR THE PREPARATION OF CRYSTALLINE FORMS OF AGOMELATINE AND NOVEL POLYMORPH THEREOF

This application is the U.S. national phase of International Application No. PCT/IB2011/003176, filed 29 Dec. 2011, which designated the U.S. and claims priority to Italy Application No. MI2011A001078, filed 15 Jun. 2011, the entire contents of each of which are hereby incorporated by reference.

SUMMARY OF THE INVENTION

The present invention concerns a new process for the preparation of two crystalline forms of agomelatine, in particular a process for the preparation of form I and a new form of agomelatine, here called form VII.

TECHNICAL BACKGROUND

Agomelatine is an antidepressant drug having the following formula (I)

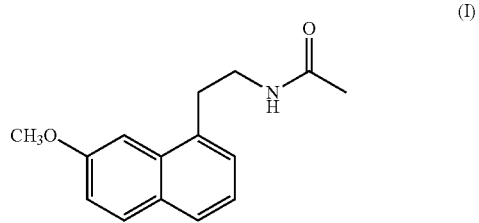

Agomelatine has been described and claimed in the patent EP0447285. In said document, agomelatine is obtained by reaction between 2-(7-methoxynaphth-1-yl)-ethylamine and acetyl chloride and classic recrystallization from isopropyl ether. The agomelatine thus obtained has a melting point of 109-110° C.; no information is provided on the type of crystalline form of the molecule.

Acta Cryst., 1994, C50, 907-910, reports for the first time a crystallographic analysis of agomelatine.

EP1564202 claims a form defined as "form II" which is obtained by reaction between 2-(7-methoxynaphth-1-yl)-ethylamine and sodium acetate and acetic anhydride in ethanol and washing of the precipitate with a water/ethanol mixture.

Said crystalline form has a melting point of 108° C. and presents specific crystallographic characteristics.

A series of successive patents describe further crystalline forms of agomelatine, in particular forms III to VI, prepared according to particular methods (crushing, atomization, crystallization in particular solvents, etc.).

EP2319827 describes a process for the preparation of crystalline form I of agomelatine which entails dissolving the agomelatine in an organic solvent miscible with water and pouring the solution thus obtained into water having a temperature equal to or below 30° C.

Also CN101704763A describes a process for the preparation of form I of agomelatine which is very similar to that of EP2319827, at a temperature of between 0° C. and 100° C.

However, the processes described in EP2319827 and CN101704763A have some drawbacks. The applicant has tried to repeat said processes and has observed that they are not reproducible with constant results, because they produce different crystalline forms and often mixtures of different crystalline forms of agomelatine.

OBJECTS OF THE INVENTION

An object of the present invention is to provide a process for preparation of the crystalline form I of agomelatine which overcomes the drawbacks of the known art and is constantly reproducible.

A further object of the invention is to provide a process for preparation of the crystalline form I of agomelatine which is industrially and economically feasible.

A further object of the present invention is to provide a process for the preparation of a new crystalline form of agomelatine, here called form VII.

DESCRIPTION OF THE INVENTION

It has now surprisingly been found that it is possible to prepare crystalline form I and the new crystalline form VII of agomelatine by means of a simple reliable process which involves the rapid cooling of a solvent containing agomelatine in solution.

Thus, according to one of its embodiments, the invention concerns a process for preparation of the crystalline form I or the new crystalline form VII of agomelatine from a solution of agomelatine in a solvent, characterized in that the agomelatine is crystallized by instantaneous precipitation from said solution at a temperature equal to or below −10° C., said solvent having a freezing point below said temperature.

By "crystalline form I of agomelatine", here otherwise called "polymorph I of agomelatine" or "agomelatine form I", we indicate the crystalline form described in Acta Cryst., 1994, C50, 907-910.

By "crystalline form VII of agomelatine", here otherwise called "polymorph VII of agomelatine" or "agomelatine form VII", we indicate the crystalline form which presents the X-ray diffraction spectrum attached to this description as FIG. 1.

In particular, the form VII of agomelatine presents the following main peaks: angle 2-Theta 9.48, 10.30, 11.84, 12.78, 13.78, 15.12, 16.08, 17.28, 18.50, 19.06, 20.80, 21.14, 23.84, 25.70, 28.47, 30.05.

The cell of the polymorph VII is monoclinic C2 with the following parameters:
a=30.940
b=9.387 beta=81.04
c=9.414 V=2702

According to a preferred embodiment of the invention, the invention concerns a process for preparation of the new crystalline form VII of agomelatine, from a solution of agomelatine in a solvent, characterized in that the agomelatine is crystallized by instantaneous precipitation of said solution at a temperature equal to or below −10° C., said solvent having a freezing point below said temperature.

The same process allows preparation of the crystalline form I of agomelatine provided that a trigger of agomelatine form I is added at the time of precipitation. "Trigger of agomelatine form I" here indicates a small quantity, for example 0.1-1.0%, of agomelatine in the crystalline form I.

The solvent used in the process of the invention must necessarily have a freezing point below the temperature at which instantaneous precipitation of the agomelatine in forms I and VII is obtained, to prevent the passage of said solvent to the solid state.

For example, according to the invention, if the agomelatine is precipitated at −12° C. a solvent must be used having a freezing point below −12° C., for example a freezing point of −15° C. or below; if the agomelatine is precipitated at −18° C. a solvent must be used having a freezing point below −18° C., for example a freezing point of −20° C. or below; if the agomelatine is precipitated at 20° C. a solvent must be used having a freezing point below −20° C., for example a freezing point of −22° C. or below; and so on.

Said solvent can be chosen for example from alcohols; ethers, for example isopropyl ether; ketones; esters; aromatic solvents, for example toluene, benzene, xylenes, etc; alkanes, for example hexane, heptane, etc; heterocyclic solvents, for example tetrahydrofuran; and their mixtures.

Particularly preferred solvents are aromatic hydrocarbons, of which toluene is a particularly advantageous solvent.

Preferably, the expression "temperature equal to or below −10° C." is a temperature equal to or below −15° C., advantageously equal to or below −18° C., even more preferably equal to or below approximately −20° C.

"Instantaneous precipitation" indicates that the solution of agomelatine is not left to cool slowly but brought to a temperature equal to or below −10° C., preferably equal to or below −18° C., abruptly. It has been observed that it is the sudden lowering of temperature that favours precipitation of form VII of the agomelatine, or of form I if a trigger of said crystalline form is present in the vessel where the crystallization occurs.

The agomelatine/solvent ratio in the solution is not critical and depends on the solvent used, advantageously it is around 10-15 litres per kg of agomelatine, for example approximately 12 litres per kg of agomelatine. Said volumes are significantly lower than the volumes used in the documents of the prior art.

According to a preferred embodiment of the invention, the sudden lowering of the temperature of the solution as defined above, necessary for precipitating form VII (or form I) of the agomelatine, can be obtained by slowly pouring said solution in a sufficiently cold environment. In this way, abrupt cooling of the solution is obtained at the same time avoiding heating of said environment, i.e. guaranteeing maintenance of the temperature suitable for precipitation of the desired crystalline forms.

Thus, for preparation of the agomelatine form VII, the solution of agomelatine, as defined above, can be poured into a suitable vessel, for example a reactor, pre-cooled to a temperature equal to or below −10° C., preferably to the temperatures given above, slowly, i.e. so as to maintain the temperature of the reactor equal to or, preferably, below −10° C., even more preferably equal to or below −18° C. According to a particularly advantageous embodiment, the reactor will contain a small quantity of the saturated solvent of agomelatine, pre-cooled to the chosen temperature.

According to a particularly advantageous embodiment, said solvent is toluene.

If desired, it is possible to use a trigger of Agomelatine form VII to favour the precipitation thereof.

For the preparation of agomelatine form I, it is sufficient to repeat the process described above using a trigger of said form I in said vessel.

"Saturated solvent of agomelatine" indicates a solution of the chosen solvent in which the maximum possible quantity of agomelatine is dissolved, at the said temperature.

The temperature of the solution of agomelatine when it is added to the vessel or reactor can be between the ambient temperature and the boiling temperature of the solvent used, for example around 40°-50° C. The optimal temperature can be easily selected by a person skilled in the art also according to the solubility of the agomelatine in said solvent.

The crystalline form VII of agomelatine constitutes a further subject of the invention, as do the pharmaceutical compositions that contain it and its use in therapy, in particular in the treatment of depression.

According to a preferred embodiment, the starting agomelatine can be prepared by acetylation of the 2-(7-methoxynaphth-1-yl)-ethylamine in an appropriate solvent and the solution resulting from the reaction after aqueous cleaning can be used as a starting solution for the process of the invention.

The solvent will in this case be a solvent having a freezing point below −10° C., advantageously equal to or below −18° C., suitable for the acetylation reaction. Said solvent can be chosen, for example, from ethers, for example isopropyl ether; ketones; esters; aromatic solvents, for example toluene, benzene, xylenes, etc; alkanes, for example hexane, heptane, etc; heterocyclic solvents, for example tetrahydrofuran; and their mixtures. Advantageously one single solvent is used.

The aromatic hydrocarbons, of which toluene is a particularly advantageous solvent, are particularly preferred solvents.

Examples of this embodiment of the invention are provided in the experimental part of the present description.

The advantages of the process of the invention with respect to the known art are evident.

The process is constantly reproducible and always provides the agomelatine in the new form VII or in the form I if the trigger is added as described above.

Furthermore, as said above, lower volumes of solvent are used, which constitutes an important technical advantage for an industrial process involving the preparation of large product quantities.

In addition, the possibility of using one single solvent instead of a mixture of organic solvent and water allows easier recovery and recycling than the recycling of combinations of solvents miscible with one another, such as those used in the prior art discussed above.

The invention will now be described better, for non-limiting illustrative purposes, by means of the following experimental examples.

Experimental examples that demonstrate the drawbacks of the known art are also provided for comparison.

EXPERIMENTAL SECTION

Example 1

Preparation of the Crystalline Form VII of Agomelatine Starting from 2-(7-methoxy-1-naphthyl)methylamine HCl Load 2000 ml of water, 250g of 2-(7-methoxy-1-naphthyl)methylamine HCl and 2500 ml of toluene in a 5 litre reactor. Stir and load 80g of ammonia at 30% in water, thus obtaining pH≥9. Stir for 1 hour, decant for 20 minutes and separate the phases. Counter-extract the aqueous phase with 250 ml of fresh toluene. Re-combine the two toluene-rich phases and wash with 500 ml of water. Discard the aqueous phases. Anhydrify the toluene phase distilling approximately 250 ml of solvent. Heat the anhydrified toluene-rich phase to 35° C. and load 120 g of triethyl amine. Load 120 g of acetic anhydride in 10 minutes; the temperature will increase to 47° C. Bring to 65° C. and maintain for 1 hour. Stop the heating_and load 1000 ml of water, stir for 20 minutes at 50° C., decant for 20 minutes and discard the aqueous phase. Wash the toluene phase at 50° C. with 1000 ml of NaHCO$_3$ 2% in water and then with 1000 ml of water. Maintain the toluene phase at 50-60° C. and load it slowly in a reactor pre-cooled to at least −20° C. and containing 400 ml of toluene pre-cooled to −20° C. saturated with agomelatine. Adjust the addition speed so as to always maintain an internal temperature of at least −20° C. At the end of the addition, leave under stirring for 10-20 minutes and then filter, washing the panel with 400 ml of cold toluene. 220 g wet of polymorphous agomelatine VII are obtained.

Example 2

Preparation of the Crystalline Form VII of Agomelatine Starting from 2-(7-methoxy-1-naphthyl)methylamine HCl Operate as described in example 1 using a trigger of agomelatine form VII in the saturated solvent at −20° C. Polymorphous agomelatine VII is obtained.

Example 3

Preparation of the Crystalline Form VII of Agomelatine Starting from 2-(7-methoxy-1-naphthyl)methylamine HCl Operate as described in example 1 using an appropriate quantity of isopropyl ether instead of toluene. Polymorphous agomelatine VII is obtained.

Example 4

Preparation of the Crystalline Form VII of Agomelatine Starting from 2-(7-methoxy-1-naphthyl)methylamine (base)

Load 120 g of triethylamine under stirring in a 5 litre reactor containing 210 g of 2-(7-methoxy-1-naphthyl)methylamine (base) in 2500 ml of toluene heated to 35° C. Load 120 g of acetic anhydride in 10 minutes; the temperature will rise to 47° C. Bring to 65° C. and maintain for 1 hour. Stop the heating and load 1000 ml of water, stir for 20 minutes at 50° C., decant for 20 minutes and discard the aqueous phase. Wash the toluene phase at 50° C. with 1000 ml of NaHCO$_3$ 2% in water and then with 1000 ml of water. Maintain the toluene phase at 50-60° C. and load it slowly in a reactor pre-cooled to at least −20° C. and containing 400 ml of toluene pre-cooled to −20° C. saturated with agomelatine. Adjust the addition speed so as to maintain the internal temperature always at least −20° C. At the end of the addition leave under stirring for 10-20 minutes and then filter, washing the panel with 400 ml of cold toluene. 220 g wet of agomelatine (polymorph VII) are obtained.

Example 5

Preparation of the Crystalline Form VII of Agomelatine from a Solution of Agomelatine Load 220 g wet of agomelatine (for example the agomelatine coming from examples 1-3 or from any other process) and 2000 ml of toluene in a 5 litre reactor. Heat to 65° C. obtaining complete dissolution. Transfer the solution to a dripper funnel provided with heating sleeve set to 65° C. and during the transfer filter the solution. Load the hot toluene solution of Agomelatine in a reactor cooled to at least −20° C. containing 400 ml of toluene pre-cooled to −20° C. saturated with agomelatine. Adjust the addition speed so as to always maintain an internal temperature of at least −20° C. At the end of the addition leave under stirring for 10-20 minutes and then filter, washing the panel with 400 ml of cold toluene. 220 g wet of polymorphous agomelatine VII in pure form are obtained.

Example 6

Preparation of the Crystalline Form VII of Agomelatine from a Solution of Agomelatine Operate as described in example 4 using, instead of toluene, an appropriate quantity of ethanol and a trigger of agomelatine form VII in the saturated solvent at −20° C. The polymorphous agomelatine VII in pure form is obtained.

Example 7

Preparation of the Crystalline Form I of Agomelatine Starting from 2-(7-methoxy-1-naphthyl)methylamine HCl Load 2000 ml of water, 250g of 2-(7-methoxy-1-naphthypmethylamine HCl and 2500 ml of toluene in a 5 litre reactor. Stir and load 80 g of ammonia at 30% in water, obtaining pH≥9. Stir for 1 hour, decant for 20 minutes and separate the phases. Counter-extract the aqueous phase with 250 ml of fresh toluene. Re-combine the two toluene-rich phases and wash with 500 ml of water. Discard the aqueous phases. Anhydrify the toluene phase distilling approximately 250 ml of solvent. Heat the anhydrified toluene-rich phase to 35° C. and load 120 g of triethyl amine. Load 120 g of acetic anhydride in 10 minutes; the temperature will rise to 47° C. Bring to 65° C. and maintain for 1 hour. Stop the heating and load 1000 ml of water, stir for 20 minutes at 50° C., decant for 20 minutes and discard the aqueous phase. Wash the toluene phase at 50° C. with 1000 ml of NaHCO$_3$ 2% in water and then with 1000 ml of water. Maintain the toluene phase at 50-60° C. and load it slowly in a reactor pre-cooled to at least −20° C. and containing 400 ml of toluene pre-cooled to at least −20° C. saturated with agomelatine and with trigger of agomelatine form I. Adjust the addition speed so as to always maintain an internal temperature of at least −20° C. At the end of the addition leave under stirring for 10-20 minutes and then filter, washing the panel with 400 ml of cold toluene. 220 g wet of polymorphous raw agomelatine I are obtained. cl Example 8

Preparation of the Crystalline Form I of Agomelatine Starting from 2-(7-methoxy-1-naphthyl)methylamine HCl Operate as described in example 7 using an appropriate quantity of hexane instead of toluene. The polymorphous agomelatine I is obtained.

Example 9

Preparation of the Crystalline Form I of Agomelatine Starting from 2-(7-methoxy-1-naphthyl)methylamine (base)

Load 120g of triethylamine under stirring in a 5 litre reactor containing 210 g of 2-(7-methoxy-1-naphthypmethylamine in 2500 ml of toluene heated to 35° C.

Load 120g of acetic anhydride in 10 minutes; the temperature will rise to 47° C. Bring to 65° C. and maintain for 1 hour.

Stop the heating and load 1000 ml of water, stir for 20 minutes at 50° C., decant for 20 minutes and discard the aqueous phase. Wash the toluene phase at 50° C. with 1000 ml of NaHCO₃ 2% in water and then with 1000 ml of water. Maintain the toluene phase at 50-60° C. and load it slowly in a reactor pre-cooled to at least −20° C. and containing 400 ml of toluene pre-cooled to at least −20° C. saturated with agomelatine and with trigger of agomelatine FORM I. Adjust the addition speed so as to maintain the internal temperature always at least −20° C. At the end of the addition leave under stirring for 10-20 minutes and then filter, washing the panel with 400 ml of cold toluene. 220 g wet of polymorphous agomelatine I are obtained.

Example 10

Preparation of the Crystalline Form I of Agomelatine from a Solution of Agomelatine Load 220 g wet of raw agomelatine (for example the agomelatine coming from examples 6-8 or from any other process) and 2000 ml of toluene in a 5 litre reactor. Heat to 65° C. obtaining complete dissolution. Transfer the solution to a dripper funnel provided with heating sleeve set to 65° C. and during the transfer filter the solution. Load the hot toluene solution of raw agomelatine in a second reactor containing 400 ml of toluene pre-cooled to −20° C. saturated with agomelatine and with trigger of agomelatine FORM I. Adjust the addition speed so as to always maintain an internal temperature of at least −20° C. At the end of the addition leave under stirring for 10-20 minutes and then filter, washing the panel with 400 ml of cold toluene. 220 g wet of polymorphous agomelatine I in pure form are obtained.

Example 11

Preparation of the Crystalline Form I of Agomelatine from a Solution of Agomelatine Operate as described in example 10 using an appropriate quantity of methyl isobutyl ketone instead of toluene. The polymorphous agomelatine I in pure form is obtained.

COMPARATIVE EXAMPLES

Examples of repetitions of the methods described in the prior art relative to the preparation of form I are given below.

Comparative Example (a)

10 g of agomelatine are dissolved in 30 ml of methanol. The solution is added dropwise to 200 ml of water at a temperature below 30° C. The crystal formed is isolated by filtering and dried in a vacuum at 30° C. A mixture of the polymorphs I and II of agomelatine is obtained.

Comparative Example (b)

10 g of agomelatine are dissolved in 50 ml of acetone. The solution is added dropwise to 1000 ml of water at a temperature below 30° C. The crystal formed is isolated by filtering and dried in a vacuum at 30° C. Polymorph II of agomelatine is obtained.

The invention claimed is:

1. A process for preparation of the crystalline form of agomelatine with the x-ray diffraction spectrum of FIG. 1 which presents the following significant peaks: angle 2-Theta 9.48, 10.30, 11.84, 12.78, 13.78, 15.12, 16.08, 17.28, 18.50, 19.06, 20.80, 21.14, 23.84, 25.70, 28.47, 30.05; from a solution of agomelatine in a solvent, characterized in that the agomelatine is crystallized by instantaneous precipitation from said solution, at a temperature equal to or below −10° C., said solution of agomelatine is poured slowly into a suitable vessel pre-cooled to a temperature equal to or below −10° C., and the resulting precipitate is isolated, said solvent having a freezing point below said temperature.

2. The process as claimed in claim 1, characterized in that said temperature is equal to or below −18° C.

3. The process as claimed in claim 2, characterized in that said temperature is equal to or below −20° C.

4. The process as claimed in claim 1, characterized in that said solvent is chosen from alcohols; ethers; ketones; esters; aromatic solvents; alkanes;

heterocyclic solvents; and their mixtures.

5. The process as claimed in claim 4, characterized in that said solvent is chosen from the aromatic hydrocarbons and their mixtures.

* * * * *